US006047411A

United States Patent [19]

[11] Patent Number: 6,047,411

[45] Date of Patent: Apr. 11, 2000

Ryden et al.

[54] POWER PACK

[75] Inventors: William Dennis Ryden, Colorado Springs; Peter Jerard Sqires, Boulder, both of Colo.

[73] Assignee: Smith Sport Optics

[21] Appl. No.: 09/012,950

[22] Filed: Jan. 23, 1998

[51] Int. Cl.[7] .......... A61F 9/02

[52] U.S. Cl. .......... 2/436; 2/171.3; 2/906; 318/432

[58] Field of Search .......... 2/436, 437, 171.3, 2/905, 906; 200/252, 43.11, 43.16, 43.19; 362/200; 318/432, 433

[56] References Cited

U.S. PATENT DOCUMENTS

| | | | |
|---|---|---|---|
| 2,714,152 | 7/1955 | Ackerman et al. | 362/200 |
| 3,377,626 | 4/1968 | Smith . | |
| 3,691,565 | 9/1972 | Galonek . | |
| 3,825,953 | 7/1974 | Hunter . | |
| 4,150,443 | 4/1979 | McNeilly | 2/436 |
| 4,443,893 | 4/1984 | Yamamoto | 2/436 |
| 4,953,963 | 9/1990 | Miller | 350/547 |
| 5,104,430 | 4/1992 | Her-Mou | 2/171.3 |
| 5,425,620 | 6/1995 | Stroud | 2/171.3 X |
| 5,452,480 | 9/1995 | Ryden | 2/436 |
| 5,542,130 | 8/1996 | Grabos, Jr. et al. | 2/436 |
| 5,780,986 | 7/1998 | Shelton et al. | 318/432 |

*Primary Examiner*—Peter Nerbun

*Attorney, Agent, or Firm*—Dale B. Halling

[57] ABSTRACT

A power pack (12) for a ventilating fan (16) of a sports goggle (10) has a housing (12) designed to attach to a strap (14) of the sports goggle (10). The housing (12) has a slider (20) that is substantially rectangular in shape and is substantially the same size as the housing (12). The slider (20) forms an outer wall of the housing (12). A power regulating circuit (100) contained in the housing (12), is designed to be connected to a battery and provide a constant voltage power supply to the ventilating fan (16).

20 Claims, 3 Drawing Sheets

POWER PACK

FIELD OF THE INVENTION

The present invention relates generally to the field of portable power sources and more particularly to a power pack.

BACKGROUND OF THE INVENTION

Sports goggles have been used to protect the user from foreign objects, sun and wind. One problem that has occurred with sports goggles is that they have a tendency to fog. Many types of sports goggles attempt to avoid this by having air vents that allow cooler, drier air to circulate through the enclosed space of the goggle. The cooler, drier air lowers the dew point of the air inside the goggle and eliminates the fog. Unfortunately, the air vents help most while the user is moving and provide very little relief once the user has stopped moving. In addition, while the user is moving the goggle len's temperature is lowered. Because the goggle len's temperature is lowered while the user is moving, the lens is more likely to fog over when the user stops moving.

Some manufactures of sports goggles have added circulating or ventilating fans in the top of their sports goggles. These ventilating fans require portable power sources. Unfortunately most portable power sources are difficult for a user to operate with gloved hands. In addition, the power regulating circuits used by these power packs tend to increase the instantaneous torque. This high instantaneous torque results in a noisy fan that is irritating to the user.

Thus there exists a need for a power pack that can be easily operated by a user with gloved hand and that tends to reduce the noise associated with the ventilating fan.

DETAILED DESCRIPTION OF THE DRAWINGS

A power pack for a ventilating fan of a sports goggle has a housing designed to attach to a strap of the sports goggle. The housing has a slider that is substantially rectangular in shape and is substantially the same size as the housing. The slider forms an outer wall of the housing. A power regulating circuit is contained in the housing. The power regulating circuit is designed to be connected to a battery and provide a constant voltage power supply to the ventilating fan. The power pack is easy for a user to operate with gloved hands. The constant voltage power supply results in a more constant torque on the fan motor and as a result a quieter fan.

Figure 1:
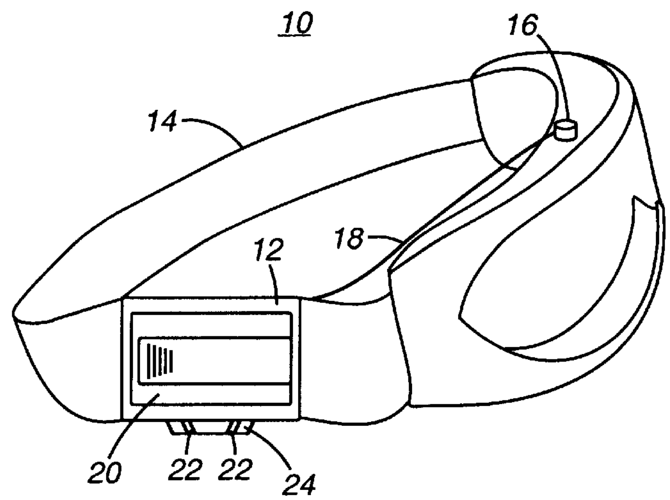
FIG. 1 is a perspective view of a sports goggle with a power pack in accordance with one embodiment of the invention.

FIG. 1 is a perspective view of a sports goggle 10 with a power pack 12 in accordance with one embodiment of the invention. The power pack 12 attaches to a strap 14 of the sports goggle. The power pack provides a constant voltage power supply to a ventilating fan 16 located in a top of the sports goggle. A wire 18 connects the power pack 12 to the fan 16. The power pack 12 has a slider 20 that slides along the same direction as the length of the strap 14. By moving the slider 20 a user can move the power pack from an off position to a low power position or a high power position. Since the slider 20 is large, it is easy to operate with a gloved hand. In addition, the power pack has a locking lever (locking mechanism) that fits inside a pair of grooves 22 of a flange 24. The locking lever allows a user to lock the power pack in an off position when the sports goggles are being stored. This prevents the power pack 12 from switching on and running out the battery when the sports goggles are thrown in a locker or trunk of a car.

Figure 2:
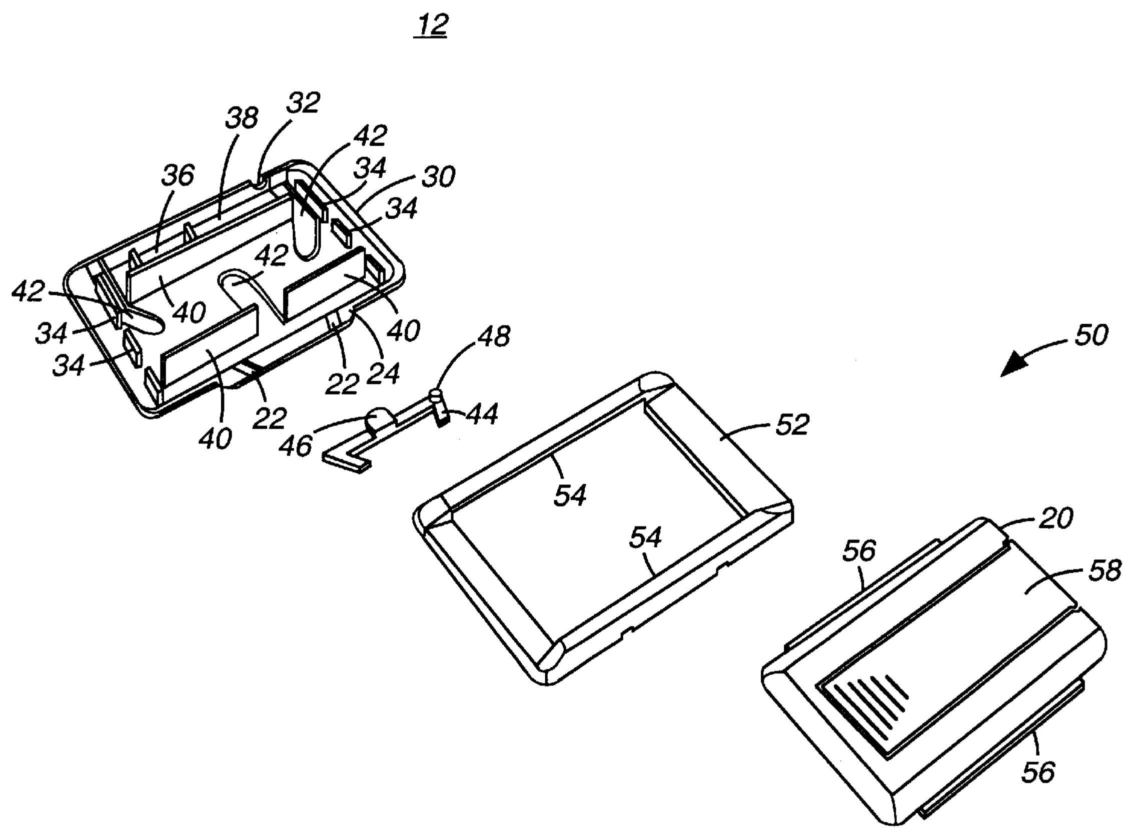
FIG. 2 is an exploded view of a power pack housing in accordance with one embodiment of the invention.

FIG. 2 is an exploded view of a power pack housing 12 in accordance with one embodiment of the invention. The housing 12 has a base 30 having a generally rectangular shape. This view shows the inside of the base 30. The base 30 has a battery LED indicator cutout 32, a plurality of battery lead flanges 34, a switch box 36, a circuit board compartment 38 and a pair of battery housing sides 40. A plurality of strap clips (attachment mechanism) 42 are formed on an outside portion of the base 30. The plurality of clips 42 are used to hold the power pack 12 to the strap 14. A locking lever 44 fits inside the pair of grooves 22 and a central portion 46 of the locking lever 44 is contained by the lower battery housing sides 40. The locking lever 44 has a pin (engaging peg) 48 that extends up from the lever arm. This pin 48 engages a slot in the slider 20 to hold the power pack in an off position. A cover 50 fits over the base 30 to form a cavity inside the battery pack housing 12. The cover 50 includes a frame 52 and the slider 20. A pair of flanges 54 are formed on opposite sides of the frame 52. A pair of blades 56 on the slider 20 slide against the pair of flanges 54 and keep the slider connected to the frame 52. The slider has a battery housing cover 58 that slides into place in a conventional manner.

Figure 3:
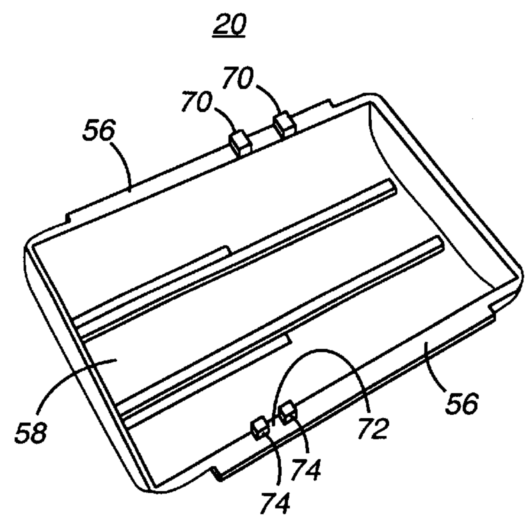
FIG. 3 is a perspective view of the interior portion of a slider in accordance with one embodiment of the invention.

FIG. 3 is a perspective view of the interior portion of a slider 20 in accordance with one embodiment of the invention. The slider 20 has a pair of switch flanges 70 that engage a switch of the power regulating circuit. As the slider 20 is moved, the switch is changed from an off position to a low position or a high position. The slider 20 also has a slot (peg slot) 72 formed by a pair of locking flanges 74. The locking flanges engage the pin 48 on the locking lever 44 to hold the power pack in an off position.

Figure 4:
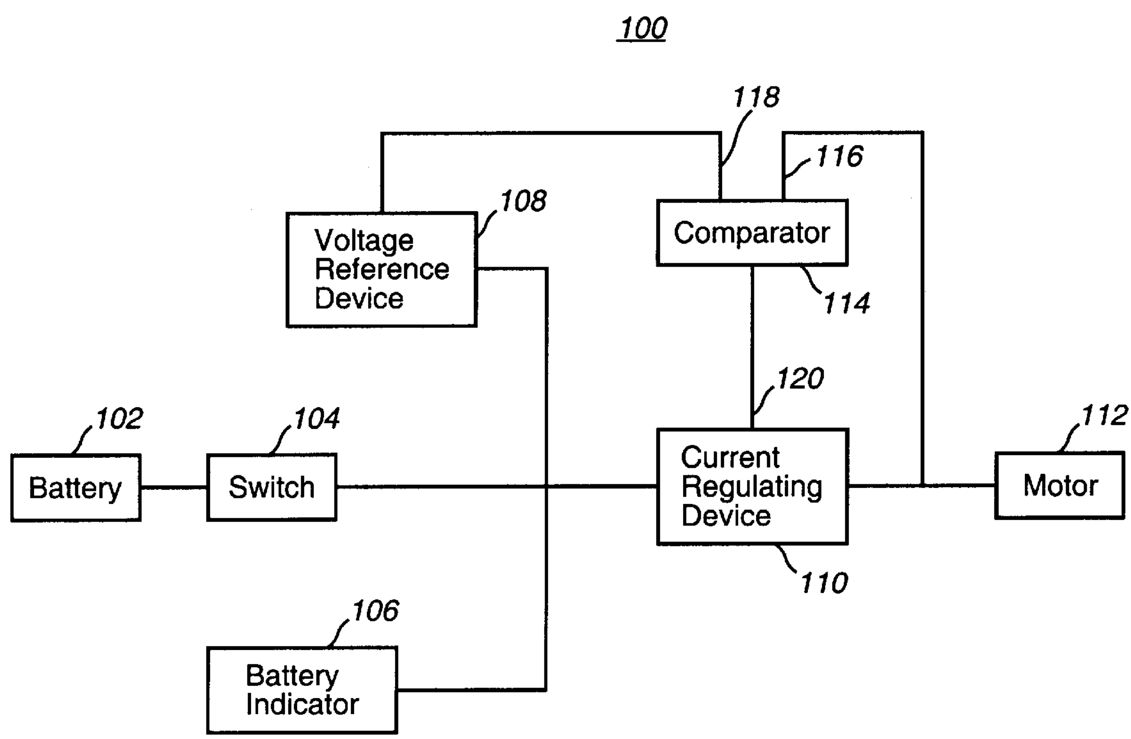
FIG. 4 is a block diagram of a power regulating circuit in accordance with one embodiment of the invention.

FIG. 4 is a block diagram of a power regulating circuit 100 in accordance with one embodiment of the invention. A battery 102 is connected to a switch 104. The switch 104 is connected to a battery charge indicator level 106, a voltage reference device 108 and a current regulating device 110. The current regulating device 110 provides a current to a motor 112 of the ventilating fan. A comparator (comparator circuit) 114 compares the voltage of the motor 116 to a reference voltage 118. When the motor voltage 116 is greater than the reference voltage 118, the comparator 114 sends a control signal to a control input 120 of the current regulating device 110 to reduce the current to the motor 112. When the motor voltage 116 is less than a reference voltage 118, the comparator sends a control signal to increase the current to the motor 112. This feedback circuit guarantees that the motor sees a constant voltage source, thus eliminating spikes in the torque of the motor that generate noise. In a preferred embodiment the voltage reference varies slightly as a function of temperature to compensate for the increase in friction of the motor at lower temperatures. The voltage reference must increase in voltage as the temperature decreases to compensate for the increase friction of the motor. In addition, the increase in voltage should match the decrease in speed of the motor due to the friction.

Figure 5:
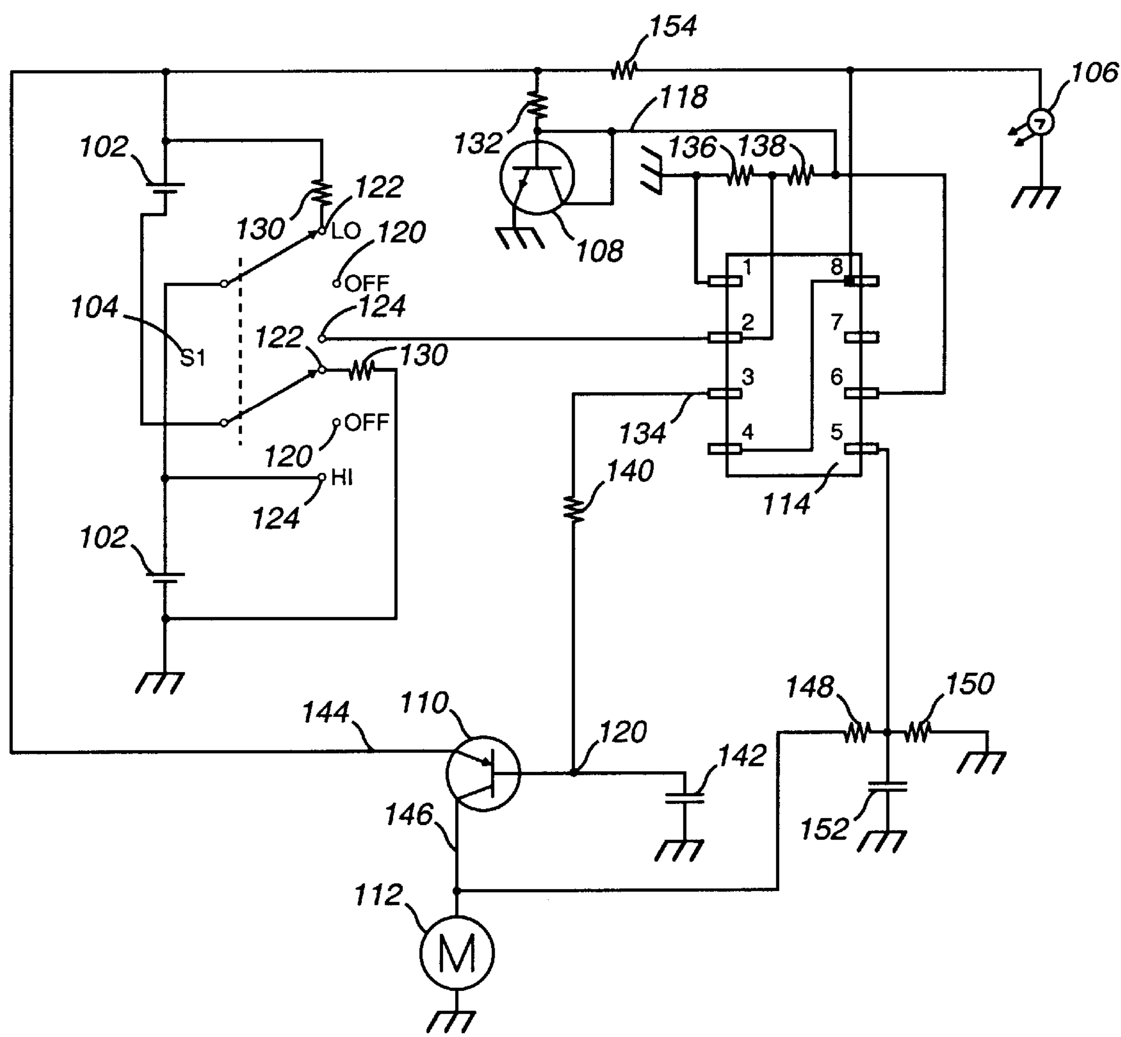
FIG. 5 is a circuit diagram of a power regulating circuit in accordance with one embodiment of the invention.

FIG. 5 is a circuit diagram of a power regulating circuit in accordance with one embodiment of the invention. In this embodiment the circuit is shown with two batteries (pair of batteries) 102. The batteries 102 are connected to a switch (three position switch) 104 that has an off position 120, a low position (parallel configuration) 122 and a high position (series configuration) 124. In the low position 122 the batteries are connected together in a parallel configuration. If a user places one of the batteries in the wrong way, this can short the batteries and lead to overheating of the batteries. However, the present circuit includes a pair of current limiting resistors 130 that limit the current to a safe level when the user places one of the batteries in the wrong way. In the high position 124 the batteries 102 are connected in series.

In the low position 122 the batteries' voltage is connected across a resistor 132 and a forward biased silicon diode (an NPN transistor with the base tied to the collector) 108. The forward biased silicon diode performs the function of a voltage reference. In addition, the forward biased silicon diode 108 has a temperature dependence that nearly matches the friction increase of the motor. The reference voltage is 0.6 volts at 21.1° Centigrade (70° Fahrenheit) and 0.67 volts at 12.2° Centigrade (10° Fahrenheit).

A 551 timer integrated circuit (TLC551 from Texas instruments) 114 is used as the voltage comparator because it is inexpensive and operates at 0.7 volts. The output of the comparator 114 is pin 3 at 134. Pin 3 is high when the voltage at pin 5 is greater than the voltage at pin 6. Note that the voltage at pin 6 is equal to the reference voltage 118. The output at pin 3 is low when one half the reference voltage 118 is greater than one half the motor voltage (pin 5). This one half has to do with the internal workings of the integrated circuit and is not relevant to the broad operation of the power regulating circuit 100. Conceptually, pin 3 is low when the reference voltage is greater than the motor voltage and pin 3 is high when the motor voltage is greater than the reference voltage. The resistors 136, 138 have the same resistance and divide the reference voltage 118 by one half. Thus the operation of the timer circuit results in the output of pin 3 134 jumping between a high voltage and a low voltage. The output of pin 3 is connected across a resistor 140 and then to the base 120 of a pnp transistor 110 and a capacitor 142 to ground. The capacitor 142 stores the voltage and evens out the on-off nature of the output from pin 3. As the voltage on the capacitor 142 increases, the current flowing from the batteries 102 through the emitter 144 to the collector 146 is reduced. As a result the voltage across the motor 112 is reduced. When the voltage across the motor falls enough, one half the voltage at pin 5 will be less than the voltage at pin 2 and the output at pin 3 will go low. This will cause the voltage across the capacitor 142 to drop, resulting in an increase in the current through the emitter 144 to the collector 146. This will increase the voltage across the motor 112. Eventually, the voltage at pin 5 will be greater than the voltage at pin 6 and the output of pin 3 will go low. Note that the integrated circuit divides the voltage of pin 5 by half before comparing it to the voltage at pin 2, as a result conceptually the same voltages are compared by pin 2—pin 5 as pin 6—pin 5. The resistors 148, 150 are selected to provide the proper motor operating speed. In one embodiment the resistors are selected so that the Namiki 6CV motor operates at 0.68 volts at 22.1° Centigrade giving a motor speed of 5500 revolution per minute (RPM). In one embodiment a capacitor 152 is inserted in the circuit between the resistor 148 and 150 to ground. The capacitor 152 has the effect of driving the voltage of pin 5 to zero upon start-up of the motor 112. This provides additional voltage at the start-up to the motor to start the motor.

In the high position 124 the batteries 102 are tied together in series. The center tap of the switch 104 is then tied to pin 2. As a result pin 2 sees the voltage of one of the batteries 102 and does not see the reference voltage 118. As a result the voltage at pin 2 is always higher than the voltage at pin 5 (motor voltage) and this causes pin 3 to always be low. When pin 3 is always low the transistor 110 is always completely open and the motor 112 has the full voltage (current) of both batteries applied at all times. In the high position 124 the voltage of the batteries 102 is dropped across the resistor 154 and an LED 106. As the battery power goes low, the LED 106 no longer lights.

Thus there has been described power pack that is easy to operate by a user with gloved hand and that tends to reduce the noise associated with the ventilating fan. While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A power back for a ventilating fan of a sports goggle, comprising:

a housing having mean s for attaching to a strap of the sports goggle, the housing having a slider, wherein the slider has substantially rectangular shape and is substantially the same size as the housing, the slider forming an outer wall of the housing; and a power regulating circuit contained in the housing, the power regulating circuit having means for connecting to a battery and provide a constant voltage power supply to the ventilating fan.

2. The power pack of claim 1, wherein the slider is attached to a switch electrically connected to the power regulating circuit.

3. The power pack of claim 2, wherein the slider is adapted for movement along a length of the housing.

4. The power pack of claim 3, further including a lock mechanism attached to the housing to prevent movement of the slider.

5. The power pack of claim 4, wherein the lock mechanism is a locking lever with an engaging peg that mates with a peg slot in the slider.

6. The power pack of claim 1, wherein the power regulating circuit has a three position switch, the three positions corresponding to an off position, a low position and a high position.

7. The power pack of claim 6, wherein the low position connects a pair of batteries in a parallel configuration.

8. The power pack of claim 6, wherein the high position connects a pair of batteries in a series configuration.

9. The power pack of claim 1, wherein the power regulating circuit further includes a comparator circuit that compares a reference voltage to a motor voltage.

10. The power pack of claim 9, wherein an output of the comparator is connected to a control input of a current regulating device.

11. The power pack of claim 10, wherein an output of the current regulating device is connected to the motor.

12. A power pack housing comprising:

a base having a substantially rectangular housing with clips on an outside of the base; and a cover fitting over the base to form a cavity, the cover having a frame, a pair of flanges formed on opposite sides of the frame and a slider having a pair of blades that glide against the pair of flanges.

13. The power pack housing of claim 12, further including a locking lever between the base and the frame, the locking lever having a protrusion that engages a slot of the slider.

14. The power pack housing of claim 12, wherein the base has an attachment mechanism for holding the power pack housing to a strap.

15. A power regulating circuit for a motor, comprising:

a switch designed to connect to a battery;

a voltage reference device connected to the switch;

a comparator connected to a reference voltage from the voltage reference device and connected to a motor voltage; and a current regulating device having a control input connected to an output of the comparator, the current regulating device having an input connected to the switch and having an output connected to the motor.

16. The power regulating circuit of claim 15, wherein the voltage reference device is a forward biased diode.

17. The power regulating circuit of claim 15, wherein the current regulating device is a transistor.

18. The power regulating circuit of claim 15, further including a battery charge level indicator.

19. The power regulating circuit of claim 15, wherein the switch is a three position switch having an off position, a parallel configuration position and a series configuration position.

20. The power regulating circuit of claim 19, further including a limiting resistor in the parallel configuration position.

* * * * *